United States Patent [19]

Stolle et al.

[11] Patent Number: 4,748,018

[45] Date of Patent: May 31, 1988

[54] METHOD OF PASSIVE IMMUNIZATION OF MAMMALS USING AVIAN ANTIBODY

[75] Inventors: Ralph J. Stolle, Oregonia, Ohio; Lee R. Beck, Birmingham, Ala.

[73] Assignee: Stolle Research & Development Corp., Lebanon, Ohio

[21] Appl. No.: 622,130

[22] Filed: Jun. 19, 1984

Related U.S. Application Data

[63] Continuation-in-part of Ser. No. 577,804, Feb. 7, 1984, abandoned.

[51] Int. Cl.[4] .................... A61K 39/40; A61K 39/395
[52] U.S. Cl. ........................................ 424/87; 424/85; 424/92
[58] Field of Search ...................................... 424/85-92

[56] References Cited

U.S. PATENT DOCUMENTS

| | | | |
|---|---|---|---|
| 3,128,230 | 4/1964 | Heinbach | 424/86 |
| 3,376,198 | 4/1968 | Petersen et al. | 424/89 |
| 4,284,623 | 8/1981 | Beck | 424/86 |
| 4,585,651 | 4/1986 | Beck et al. | 424/89 |

FOREIGN PATENT DOCUMENTS

1442283 7/1976 United Kingdom .

OTHER PUBLICATIONS

Lebacq-Verheyden, A., et al., Immunology, 27: 683–692 (1974).
Leslie, G. A., et al., Journal of Medicine, 130: 1337–1351 (1969).
Polson, A.; et al., Immunological Communications, 9: 494–514 (1980).
Fertel, R., et al., Biochemical and Biophysical Research Communications 102: 1028–1033 (1981).
Jensenius, J. C., et al., Journal of Immunological Methods, 46: 363–368 (1981).
Polson, A., et al., Immunological Communications, 9: 475–493 (1980).

*Primary Examiner*—Blondel Hazel
*Attorney, Agent, or Firm*—Saidman, Sterne, Kessler & Goldstein

[57] ABSTRACT

A method of passively immunizing a mammal against a condition caused by an antigen comprising: administering to the mammal immunizing amounts of an antibody obtained from a domesticated fowl which has been immunized against the antigen; the mammal being tolerant to the antibody by virtue of having a history of consumption of antibody containing material derived from the egg of a fowl.

25 Claims, No Drawings

METHOD OF PASSIVE IMMUNIZATION OF MAMMALS USING AVIAN ANTIBODY

The present application is a continuation-in-part of application Ser. No. 577,804, filed Feb. 7, 1984, now abandoned.

FIELD OF THE INVENTION

The present invention relates to a method for passively immunizing a mammal with heterologous antibody obtained from an immunized domesticated fowl species.

DESCRIPTION OF THE BACKGROUND ART

It is well known to those skilled in the art of immunology that serum globulin fractions consisting of various antibody types such as IgA, IgM, and IgG, can be used to counter the corresponding antigens, thereby neutralizing the harmful effects of the antigens. The various antigens include carcinogenic, bacterial and viral species, and bioregulatory factors of plant and animal origin, as well as toxins and poisons.

Normally, upon exposure to a foreign antigen, the immune system of an animal will neutralize the bioregulatory and/or harmful effects of the antigen. The exposure of the immune system of a given mammal to foreign antigens can occur either naturally, or the host may be exposed to the antigen by the intentional administration of antigen in the form of a vaccine. When an animal is vaccinated with an antigenic substance, an immune response results in which the subject produces antibodies. This process is generally referred to as active immunization of the host species exposed to antigen. The antibodies produced by any given species of animal by the process of active immunization are homologous antibodies to said given species of animal.

It is well known that antibody produced in one species can be used to neutralize the effects of the corresponding antigen in other species. Passive immunization occurs when an individual from one species receives immune protection from antibodies produced in an individual of another species. This process requires the transfer of antibodies from a donor to a recipient. If the donor and recipient are of the same species the antibodies are homologous. On the other hand, if the donor and recipient are of different species, the antibodies are said to be heterologous.

Although it is known that passive immunization provides an effective method for the prevention and treatment of disease, the use of passive immunization in human medicine is limited because homologous human antibody formulations are not generally available. On the other hand, passive immunization of humans with heterologous antibodies produced in a donor animal species is employed only in situations of emergency because the use of heterologous antibodies can be dangerous. Examples of situations where heterologous antibodies are employed in human treatment include the use of snake venom and bee-venom antisera which are produced in horses. These antibodies neutralize the snake and bee toxins, thereby eliminating and/or reducing the harmful effects thereof.

Passive immunization of humans with heterologous antibodies is not safe because antibodies of non-human origin are foreign to the human immune system. Exposure of the recipient's immune system to the foreign donor antibody protein produces an immune reaction in the recipient against the foreign antibody. The immune response causes serum sickness, which can lead to anaphylactic shock and death. Therefore, despite the known and beneficial use of heterologous antibodies, this method of treatment is not generally employed because of safety considerations.

It is known that domestic avian species such as chickens, turkeys and ducks produce antibodies in the blood and eggs against factors which cause avian diseases, as well as against other antigens. For example, LeBacq-Verheyden, et al., *Immunology*, 27:683 (1974), and Nestle, G. A., et al., *J. Med.*, 130:1337 (1969) have quantitatively analyzed immunoglobulins of the chicken. Polson, A., et al., *Immunological Communications*, 9:495–514 (1980), immunized hens against several proteins and natural mixtures of proteins, and detected IgY antibodies in the yolk of the eggs. Fertel, R., et al., *Biochemical and Biophysical Research Communications*, 102:1028–1033 (1981) immunized hens against prostaglandins and detected antibodies in the egg yolk. Jencenius, et al., *Journal of Immunological Methods*, 46:363–68 (1981) provide a method of isolating egg yolk IgG for use in immunodiagnostics. Polson, A., et al., *Immunological Communications*, 9:475–493 (1980) describe antibodies isolated from the yolk of hens that were immunized with a variety of plant viruses.

All of these references, however, relate only to studies of fowl immunoglobulins raised against various antigens, not all of them specifically affecting or causing mammalian diseases or conditions. As noted, Polson (both papers, 1980) or Jencenius supra, suggest the use of avian antibodies instead of mammalian antibodies as tools in diagnostic procedures. Polson, *Immunological Communications*, 475–493 (1980) suggests, on page 491, that it might be possible to protect newly hatched chickens passively against diseases to which their mothers were not exposed by injection of the chicks with yolk IgY derived from hens that were hyperimmunized against the diseases. This suggestion, in addition to being speculative, deals solely with homologous passive immunization of one species with the antibody obtained from the same species, albeit, a different individual.

Jencenius, et al., *Journal of Immunological Methods* 46, supra, states at page 67 that "one may even speculate that, by providing large amounts of neatly wrapped antibody, eggs from suitable immunized chickens might be a useful and harmless therapy for some intestinal infections, if steps can be taken to minimize the degradation of the antibody by intestinal proteolytic enzymes." The authors analogize this to the idea of treating infections with milk from immunized animals, citing the work of Campbell, et al., *Journal of Immune Milk*, 1:3 (1964). The suggestion in Jencenius et al., is, by its own admission, speculative. In addition, it is accompanied by the warning that the antibody would be degraded by intestinal proteolytic enzymes.

The phylogenetic distance between birds and mammals have made the chicken and other domesticated fowl an illogical choice for producing antibodies against mammalian diseases or conditions. The obvious choice of antibodies for immune therapeutic products intended for the treatment of mammalian species has been another mammal having a close biogenetic relationship. For example, it would not be logical to treat human subjects with chicken antibody administered in a parenteral dose formulation, because chicken protein is foreign to the human immune system, and would cause allergic reactions with repeated use. Indeed, there is no evidence in the scientific literature that antibodies derived from bird eggs have been used in preventing or treating conditions in mammals.

SUMMARY OF THE INVENTION

The present invention provides a method of administering a heterologous low antigenic protein formulation to a subject under conditions which avoid scrum sickness or anaphylactic shock. It also provides a method of administering a heterologous, low antigenic IgG formulation obtained from the sera and/or food products of an immunized domesticated fowl to a subject under conditions which avoid serum sickness or anaphylactic shock.

The invention thus comprises a method of heterologous passive immunization of a mammal against a condition caused by an antigen which comprises: administering to said mammal an immunologically effective amount of an antibody obtained from a domesticated fowl which has been immunized against said antigen; said mammal being tolerant to said antibody by virtue of having a history of consuming material derived from the egg of said fowl, as a food source.

The present invention is a further development over the invention disclosed and claimed in application Ser. No. 577,804, filed Feb. 4, 1984 at the U.S. Patent and Trademark Office by Beck and Stolle, for "Heterologous Protein Antibody Formulation for Passive Immunization." The entire disclosure of said application is herein incorporated by reference.

In Ser. No. 577,804, is claimed a method of passive immunization of a mammal which comprises parenterally injecting a purified heterologous antibody obtained from the milk of a bovid, which bovid has been immunized against an antigenic substance, and wherein the mammal has a history of consumption of milk from such domesticated bovid. In the same application is also disclosed a method of passive immunization of a mammal which comprises parenterally injecting a purified heterologous antibody obtained from the eggs of a domesticated fowl, which species has been immunized against an antigenic substance, and wherein the mammal has a history of consumption of eggs from such domesticated fowl.

The present invention expands on the concepts disclosed in Ser. No. 577,804 in that administration of the egg antibody can be by any appropriate route, not only parenteral.

In a further embodiment, the present invention also comprises a method of heterologous passive immunization of a mammal against a condition caused by an antigen which comprises:

(a) feeding said mammal a material having an enhanced antibody titer against said antigen obtained from the egg of a domesticated fowl immunized against said antigen, until said mammal develops substantial tolerance to said antibodies; and (b) administering to said mammal an immunologically effective amount of an antibody obtained from a domesticated fowl immunized against said antigen.

Thus, in this embodiment, prior to the administration to the mammal of antibodies obtained from a domesticated fowl, the mammal is fed a material derived from eggs of a fowl immunized against the antigen.

The present invention also relates to various methods of administration, various conditions, as well as various compositions of matter useful therein.

For example, in a preferred embodiment, the present invention relates to a composition comprising:

(a) a material having an enhanced antibody titer against a given mammalian antigen, obtained from the egg of a domesticated fowl immunized against said antigen; together with (b) a material having an enhanced antibody titer against said antigen obtained from the milk of a domesticated bovid immunized against said antigen.

In another aspect of the invention, there is also provided a composition comprising:

(a) antibody purified from the egg of a domesticated fowl immunized against a given mammalian antigen together with (b) antibody purified from the milk of a bovid immunized against said antigen. The invention also comprises a composition comprising:

(a) a parenteral carrier and (b) an antibody purified from the egg of a domestic fowl which has been immunized against an antigen, said antibody not resulting in serum sickness or anaphylactic shock in the subject administered the antibody.

DETAILED DESCRIPTION OF THE PREFERRED EMBODIMENTS

The failure of the immune system of an animal to respond to foreign protein is a condition known as immunological tolerance. Moreover, it is well known to those skilled in the art of immunology that mammals of a given species lack tolerance to antibodies from various animal species, including other mammalian species. It is therefore apparent that heterologous antibodies obtained from alien species cannot be safely used to treat mammals. The discovery of the present invention is an exception to this generally accepted view of heterologous immunology. It has been discovered that the immune system of a mammal can become tolerant to heterologous antibody found in the serum or egg products of domesticated fowl. This tolerance occurs in mammalian individuals who have been previously fed a material containing antibodies from the heterologous fowl species. Individuals who have not been fed material that contain antibodies from heterologous domesticated fowl lack tolerance to the subsequently administered fowl antibody.

Thus, the essential feature of the present invention is that heterologous antibody which is obtained from the serum or egg products of domesticated fowl which have been specifically immunized against various antigens can be passively administered to a mammalian species by such administration as oral, intraperitoneal or parenteral administration (i.e., intravenous or intramuscular), without causing serum sickness or anaphylactic reactions.

As explained above, the immune system tolerance, which is a necessary condition for heterologous antibody administration, does not occur naturally, and must be built up in a mammal subject over time by the feeding of material containing fowl antibodies.

Any mammal can be treated according to the methods of the present invention. These include such domesticated mammalian species as rabbits, cows, horses, goats, sheep, and other such species used in animal husbandry. Non-domesticated mammals, such as monkeys or apes, can also be treated. Finally, the invention is applicable to the passive heterologous immunization of human beings.

Any antigen or combination of antigens may be employed. The antigen can be bacterial, viral, cellular, or any other substance to which the immune system of a domesticated fowl will respond, and which will induce a state of immune sensitivity in the fowl. The antigens are preferably those that cause various conditions in mammalian species, such as microorganisms or virus induced infections, poisonous conditions and the like. Suitable examples of bacterial antigens include *Pseudomonas aeruginosa, Pseudomonas maltophiia, Streptococcus equisimili, Streptococcus dysgalactiae, Streptococcus uberis, Streptococcus bovis, Pasteurella multocida, Pasteurella haemolytica, Moraxella bovis, Actinobacillus lignieresi, Corynebacterium renale, Fusobacterium necrophorum, Bacillus cerus, Salmonella dublin, Salmonella heidelberg, Salmonella paratyphi, Yersinia enterocolitica, Staphylococcus aureus, Staphylococcus epidermidis, Streptococcus pyogenes, Aerobacter aerogenes, Escherichia coli, Salmonella enteritidis, Klebsiella pneumoniae, Salmonella typhimurium, Haemophilus influenzae, Streptococcus viridans, Proteus vulgaris, Shigella dysenteriae,* Streptococcus, Group B, *Diploccocus pneumoniae, Streptococcus mutans,* Corynebacterium, Acne, Types 1 and 3, and the like, *Neisseria gonorrhea, Mycobacterium tuberculosis, Haemophilus vaginalis,* Group b *Streptococcus ecoli, Microplasma hominis, Hemophilus dycreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis, Chlamydia psittaci, Actinobacillus equuli, Salmonella abortus ovis, Salmonella abortus equi, Corynebacterium equi, Corynebacterium pyogenes, Actinobaccilus seminis, Mycoplasma bovigenitalium, Clostridium tetani,* and the like.

Suitable viral antigens include Equine herpes virus, Equine arteritis virus, IBR-IBP virus, BVD-MD virus, Herpes virus (humonis types 1 and 2), and the like.

Typical polypeptides are proteins affecting mammals in which passive immunization is useful. They include bioregulatory factors, hormones, enzymes, snake venoms, bee venoms, toxins and other insect and reptilian venoms.

In order to develop a tolerance for avian antibody protein in a mammal, material having a significant, tolerance-inducing amount of antibody titer against the antigen obtained from the food product of a domesticated fowl immunized against the antigen is fed the mammal until the mammal develops substantial tolerance to the antibody. Normally, this is accomplished by providing a diet containing egg material which must be consumed on a periodic basis for at least about two weeks to several months. For younger animals or humans, the minimum time period can be as short as about 10–14 days. For older animals and humans, the minimum time to acquire tolerance can be up to several months. In a preferred embodiment, the antibody titer in the material is enhanced over normal levels thereof by previous immunization of the fowl.

The tolerance of the immune system of a mammalian subject to alien antibody can be simply demonstrated by the lack of induced serum sickness of anaphylactic shock in such egg consuming subject when injected with purified fowl antibody, either intravenously or intramuscularly on repeated occasions. A safe indication that tolerance has occurred is to slowly increase the dose of the avian antibody. Lack of tolerance will be accompanied by immune reactions in the host at the site of the injection. If this happens, treatment should be discontinued. If the administration is oral, lack of tolerance will cause gastrointestinal distress.

The material fed to the mammal should be normal eggs or may have an enhanced titer against the given antigen. The material can either be whole eggs, or fractions thereof, such as the egg yolk, where most avian antibodies tend to concentrate. In addition, the material should be fed under conditions such that the avian antibody present in the material has not lost its immunogenic effect, more specifically, that the avian antibody therein should not have become denatured. Thus, if eggs are fed to the mammalian subject, the same should not be in a condition where protein has denatured.

It is known that most avian eggs contain antibodies therein against a host of naturally occuring antigens affecting domesticated fowl. In the present invention, such eggs can be fed to the mammal to induce tolerance. On the other hand, the antibody titer in the eggs fed to the mammal may also be above that of normally occurring antibodies in the domesticated fowl egg. In such case, the antibodies are, in most instances, immunologically reactive with antigens which cause conditions which are specific to the mammalian, not the avian species. Although the naturally occuring antibodies present in the yolk of non-immunized domesticated fowl, do not have specificity against antigens causing conditions in the mammalian species, they nevertheless still serve to induce immune tolerance.

By "enhanced titer" as used in the present disclosure and claims, is meant to include avian antibody titer levels against antigens which are at least 100% higher than the normal background levels of avian antibody titers against the same antigen.

Domesticated fowl which can serve as sources of eggs include chickens, turkeys, ducks, geese, and the like, most preferably chickens.

Once tolerance has been achieved in the mammalian subject, the same is ready for administration of avian antibodies having immune reactivity to a given antigen. Administration can be by any of a variety of routes, but is preferably by oral administration or parenteral injection, such as by intravenous, intraperitoneal or intramuscular injection. Oral administration of the antibody can also be effectively used to treat diseases of the mouth and gastrointestinal tract.

Immune tolerance previously developed in the subject as a result of egg consumption renders safe and effective the passive immunization using fowl antibodies. The antibodies are preferably purified by means well known in the art, such as precipitation, extraction, chromatography, fractionation, and the like. By "purified" is meant to include any avian antibody which is substantially free of other, possibly immunogenic, protein or non-protein components of avian origin. Such components may include but are not limited to other proteins, e.g. antibodies, cells, cellular fragments, membrane fragments, lipids, nucleic acids, organelles, and the like.

The avian antibody to be administered to the mammalian subject after tolerance development, can be obtained from the serum of the domesticated fowl or it can be obtained, preferably from eggs thereof. The antibody is administered directly as is, or is combined with a conventional pharmaceutically acceptable liquid or solid carrier. Most commonly, when administered by parenteral injection it is administered as a liquid formulation. The antibody can also be prepared in microparticulate form in an organic matrix material, and then directly injected into a subject.

Administration of the antibody is to be carried out in an amount which is immunologically effective for a given condition of the mammalian subject. For example, those of skill in the art can readily ascertain the amount of passively administered avian antibody to a mammalian subject affected with a given condition, such as a snake or bee bite, other insect or reptilian bites. Typical passive immunizations of this type are in the range of from 0.25 mg/kg to 1.00 mg/kg per administration. Duration and intensity of the treatment will depend on the particular condition of the subject. These conditions include not only paliative treatments, such as the treatment of a given infection, disease or poisonous state, but also include preventive treatments such as caries control. Typical administrations for preventive treatment of infectious diseases will range from about 0.25 mg/kg to 1.00 mg/kg, preferably 0.5 mg/kg to 0.75 mg/kg.

The domesticated fowl from which the egg material fed to the subject is obtained may or may not be the same fowl individual from which the antibody (preferably, purified antibody) is obtained which is administered to the (now tolerant) mammalian subject.

The following is an example of the procedure used to bring a domesticated fowl into a state of immunity.

(1) Antigen selection.
(2) Sensitization of the domesticated fowl by primary immunization.
(3) Testing the serum or eggs of the fowl to confirm sensitivity induction.
(4) Administration of boosters of appropriate dosage to induce and maintain an antibody producing state.
(5) Testing the antibody level in the egg yolk.
(6) Collecting eggs from the fowl during its immunized state.

Specific comments about various of these steps will now be given.

In step 2, the preferred method of immunization is by intramuscular injection. However, other methods such as intravenous injection, intraperitoneal injection, oral administration, rectal suppository, and the like can be used, provided the usage is sufficient to induce sensitivity. In fact, a preferred method of immunization is a procedure wherein an antigenic substance is incorporated in a microparticle of a biodegradable and biocompatible matrix material and administered by intramuscular injection into the fowl. The dosage is normally $1 \times 10^6$ to $1 \times 10^{20}$ cells, preferably $10^8$ cells to $10^{10}$ cells, most preferably $2 \times 10^8$ cells.

Step 3 is to determine whether or not the fowl has become sensitive to the antigen. There are a number of methods known to those skilled in the art of immunology to test for sensitivity (see *Methods in Immunology and Immunochemistry*, William, C. A., WM Academic Press, London (Vol. 1-5) (1977)). Examples of these include skin sensitivity tests, serum tests for the presence of antibodies to the stimulating antigens, and tests designed to evaluate the ability of immune cells from the host to respond to the antigen. The type of test employed will depend to a large extent on the nature of the antigen used. The preferred method is to use a polyvalent vaccine consisting of multiple material species as the antigen, and to test for the presence of agglutinating antibodies in the serum of the fowl before and after the challenge with the vaccine. The appearance of egg antibodies after immunization with a vaccine is indicative of sensitivity, and at this point it is possible to proceed to step 4. The minimum dose antigen necessary to induce sensitivity depends on the antigen used.

Step 4 involves the induction and maintenance of the antibody producing state. Once a fowl has been shown to be sensitized, this state is induced by repeated booster administrations of an appropriate dosage at fixed time intervals. The spacing of the administration depends on the nature of the antigen. A two week booster interval is optimal for polyvalent antigens. The booster administrations must not induce a state of immune tolerance. This would cause the fowl to pass from an antibody producing state to a state of immune tolerance to the antigen, in which case the fowl will cease to produce the antibody.

It might also be possible, for example, to use a combination of different immunization procedures, i.e., intramuscular injection for primary immunization and intravenous injection for booster injections, etc. Many different combinations of immunization methods might be employed by those skilled in the art to (1) sensitize and (2) induce the antibody producing state.

Step 5 involves the testing of egg samples from the immunized flow while the animal is in the antibody producing state for the purpose of determining the antibody level in the egg. The antibody level can be determined by well known radioimmunoassay and enzyme linked techniques.

Step 6 is the collection of eggs from the immunized fowl. The eggs can be used in the feeding stage of the invention or as sources for the purified antibody in the administration stage of the invention.

When antibody to be administered in the administration phase is obtained from serum of fowl, well known isolation and purification procedures can be utilized.

Following sterilization of the antibody by filtration, the mammalian subject is administered antibody by methods described previously for a time sufficient to provide effective treatment for the given condition. The injection site should not swell or give other evidence of an immune reaction against the injected antibody.

In a preferred embodiment of the present invention, the feeding and/or administration steps are carried out with a combination of materials. For example, feeding can be with a material or a composition of a material having an enhanced antibody titer against a given antigen obtained from the egg of a domesticated fowl immunized against the antigen, together with material having an enhanced antibody titer against the antigen obtained from the milk of a bovid immunized against the antigen. (For preparation of immune milk containing enhanced antibody titer levels see, for example, Heinbach, U.S. Pat. No. 3,128,230 and Peterson, U.S. Pat. No. 3,376,198). Thus, compositions which include such materials as hereinabove described are also included in the present invention.

In another preferred embodiment, the mammalian subject may be administered a combination of purified antibodies, one component of such a composition being an antibody obtained from a domesticated fowl immunized against a given antigen, and the other component being an antibody obtained from a bovid immunized against a given antigen.

Most preferably, a composition comprises an immunologically effective amount of a combination of antibodies, a first such antibody obtained, and possibly substantially purified from the egg of a domesticated fowl immunized against a given antigen, and a second antibody obtained, and possibly substantially purified from the milk of a domesticated bovid which has been immunized against said antigen.

The compositions described can be utilized therapeutically or in the form of premixed food products. In one embodiment, dehydrated immune milk and dehydrated immune egg materials can be mixed and used either in the feeding stage or, if the antibodies are purified, in the administration stage.

Having now generally described this invention, the same will become better understood by reference to certain specific examples which are included herein for purposes of illustration only and are not intended to be limiting unless otherwise specified.

EXAMPLE 1

The methods used to immunize chickens to produce antibodies in the eggs are similar to those used to immunize mammals, and are well known to those skilled in the art. The general procedure is to administer the vaccine by injection into the breast muscle. A preferred method is to administer 1 to 5 mg of the antigen in 1 cc of saline. The injection is repeated once each week for four weeks. Maximum antibody titers occur after the fourth injection. Antibody titers can be maintained by giving booster injections of the antigen at one to two week intervals.

By way of a specific example, a vaccine was prepared from the bacterial species listed in Table I:

TABLE I

|   | ATCC # |
|---|--------|
| 1. Strep. mutans | 27351 |
| 2. Strep. mutans | 27352 |
| 3. Strep. mutans | 27607 |
| 4. Strep. mutans | 27947 |
| 5. Strep. mutans | 31341 |
| 6. Strep. mutans | 31377 |

1. The American Type Culture Collection (ATCC) bacterial culture was reconstituted with 15 ml media and incubated overnight at 37° C.

2. Once good growth was obtained, approximately half of the bacterial suspension was used to inoculate one liter of broth, which was incubated at 37° C. The remaining suspension was transferred to sterile glycerol tubes and stored at −20° C. for up to six months.

3. After good growth was visible in liter culture, the bacterial cells were harvested by centrifuging the suspension for twenty minutes at 14,000 x to remove the media. The pellet was resuspended in sterile saline and centrifuged three times to wash the media from the cells. After the third saline spin, the pellet was resuspended in a small amount of double distilled water.

4. The media-free bacterial suspension was heat-killed by placing it in a glass flask in an 80° water bath overnight. A small amount of the heat-killed bacteria was inoculated into a broth culture to determine the viability of the growth. Bacteria must be killed for use in the vaccine.

5. Heat-killed bacteria were lyophilized and stored in sterile vials at −20° C.

6. The mixed bacterial strain was used to immunize 10 adult hen chickens. The immunization procedure was as follows: 350 mg of dry bacterial was mixed with one liter of sterile saline to a concentration of $2.2 \times 10^8$ bacterial cells/ml saline (1.0 optical density reading at 660 nm). One milliliter of this mixture was injected biweekly to the breast of chickens.

Eggs collected from the immunized chickens were processed by the following steps to obtain antibody from the egg yolks:

1. The egg yolk was separated from the white and the yolk membrane cut open and removed; 200 ml of yolk was measured and diluted with 800 ml of Tris-Buffered Suline (TBS) TBS: Tris hydroxymethylaminomethane-buffered saline: 0.14M NaCl, 0.01M Tris HCl, pH 7.4, 0.1% $NaN_3$.

2. The solution was stirred slowly at room temperature for 20 minutes. (The entire procedure was carried out at room temperature).

3. The yolk suspension was centrifuged at 14,000 x at 20° C. for 30 minutes. The precipitate was discarded.

4. One hundred ml of dextran sulphate 10% (w/v) (Sigma) in TBS, was added to the supernatant and stirred slowly for 5 minutes.

5. Two hundred fifty ml of 1M $CaCl_2$ was added and the solution incubated for 30 minutes to induce precipitation of excess dextran sulphate.

6. The suspension was centrifuged, and the supernatant put in reserve. The sediment was washed with 2000 ml of TBS to extract any protein carried with it. The two supernatants were then pooled.

7. The supernatants were dialyzed extensively against deionized water to remove salt, and lyophilized.

The egg antibody obtained from eggs before and after immunization was reacted against the bacterial vaccine using an enzyme-linked immunoassay method to determine the presence of antibodies in the chicken eggs that react specifically with the S. mutans bacteria.

The results are shown in Table II.

TABLE II

| Chick-en # | Preimmunization S. mutans Strain # | | | | | | | Postimmunization S. mutans Strain # | | | | | | |
|---|---|---|---|---|---|---|---|---|---|---|---|---|---|---|
|  | 1 | 2 | 3 | 4 | 5 | 6 | 7 | 1 | 2 | 3 | 4 | 5 | 6 | 7 |
| 1 | − | − | − | − | − | − | − | + | + | + | + | + | + | + |
| 2 | − | − | − | − | − | − | − | + | + | + | + | + | + | + |
| 3 | − | − | − | − | − | − | − | + | + | + | + | + | + | + |
| 4 | − | − | − | − | − | − | − | + | + | + | + | + | + | + |
| 5 | − | − | − | − | − | − | − | + | + | + | + | + | + | + |
| 6 | − | − | − | − | − | − | − | + | + | + | + | + | + | + |
| 7 | − | − | − | − | − | − | − | + | + | + | + | + | + | + |
| 8 | − | − | − | − | − | − | − | + | + | + | + | + | + | + |
| 9 | − | − | − | − | − | − | − | + | + | + | + | + | + | + |
| 10 | − | − | − | − | − | − | − | + | + | + | + | + | + | + |

The results from this experiment show that chickens immunized against factors that cause disease in mammals, i.e., S. mutans, produce eggs that contain antibodies that react specifically against these factors, and that eggs obtained from non-immunized chickens lack the same antibodies.

The titers of antibody against S. mutans are at least 100% greater than the background titers from non-immune eggs.

EXAMPLE 2

Avian antibody obtained from the yolk of hen's eggs immunized against the bacterial strains listed in Table I was administered to rabbits by intramuscular injection. Five mg of the hen yolk IgG dissolved in 1 cc of physiological saline was injected into the hind legs of 5 rabbits. A second injection was repeated 14 days later. Blood samples werer collected from the rabbits before and after the treatment. Serum from the rabbit samples was reacted with hen egg yolk IgG using the Outcherlony gel diffusion method to test for the presence of rabbit antibody against hen yolk IgG. The presence of rabbit antibody against hen yolk IgG provided immunological evidence that the treatment caused immunological sensitization of the rabbit immune system against chicken IgG.

The results from this experiment are shown in Table III. Presence (+) or absence (O) of antibodies in rabbit serum against chicken IgG before (0 week) and after treatment (1, 2, 3 weeks).

TABLE III

| Rabbit # | 0 Week | 1st Week | 2nd Week | 3rd Week |
|---|---|---|---|---|
| 1 | 0 | 0 | + | + |
| 2 | 0 | 0 | + | + |
| 3 | 0 | + | + | + |
| 4 | 0 | 0 | + | + |
| 5 | 0 | + | + | + |

None of the five rabbits had antibodies in their blood against chicken IgG prior to treatment. By two weeks post treatment, the five rabbits had high antibody tilters in their blood against chicken IgG. This experiment shows that treatment of the rabbits with chicken IgG obtained from immunized chickens caused immune sensitization of the rabbits. Subsequent treatment of the five rabbits having positive tilters by inrtravenous injections of 5 mg of the antibody caused anaphylactic reaction and death of all five rabbits.

The experiment thus confirmed the contemporary knowledge that antibody obtained from an avian species causes allergic reactions when administered by repeated injections to a mammalian species.

The next step in the experiment illustrated the basis of this invention. The identical rabbit experiment described above was repeated. However, in this experiment, the five rabbits were fed one egg obtained from immunized chickens dissolved in 50 cc of water for 30 consecutive days prior to injecting the identical dose of antibody obtained from eggs of immunized chickens. The results of this experiment are shown in Table IV.

Presence (+) or absence (O) of antibodies in rabbit serum against egg IgG before (0 Week) and after treatment (1, 2, 3 weeks).

TABLE IV

| Rabbit # | 0 Week | 1st Week | 2nd Week | 3rd Week |
|---|---|---|---|---|
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |

None of the five rabbits had antibody in their blood against hen yolk antibody either before or after treatment. Moreover, there were no ill effects in these rabbits when chicken antibody obtained from immunized chickens was administered by intravenous injection. These experiments led to the conclusion that oral consumption of immune hen eggs by the rabbits makes the rabbits tolerant to immune hen IgG.

EXAMPLE 3

The purpose of the present experiment is to demonstrate that treatment of a mammal with avian antibody can indeed serve a useful purpose. For this demonstration the rat was chosen as an example of a mammalian species, and the chicken as an example of the avian antibody producer. In Beck et al., U.S. Pat. No. 4,324,782, a rat model was used to demonstrate the utility of an antibody of mammalian origin (cow milk) to control Streptococcus mutans infections of rats. The purpose of the present experiment is to demonstrate that chicken egg antibody has the same utility for treating the same diseases as cow antibody.

For the present experiment one serotype strain of Streptococcus mutans and three groups of experimental germfree rats (10 rats/group) were used. Group 1 was fed regular cariogenic diet #305; group 2 was fed diet #305 plus immune chicken IgG; and group 3 was fed diet #305 plus non-immune chicken IgG. In this experiment, weanling rats (age 20 days) were transferred to an experimental isolator, infected with virulent S. mutans, and provided diet ad libitum. Animals were removed from the experiment at the age of 45 days (total time 25 days). At the termination of the experiment, rats were removed from the isolator and weighed. The mandibular molars were removed and asceptically defleshed. They were immediately placed in tubes containing phosphate buffered saline (PBS), treated by sonication, diluted and plated in duplicate (three different dilutions) on blood and Mitis salivarius. The results from this experiment are shown in Table V.

TABLE V

| | Mean Caries Scores[a] | | | | | | | | | | | | Mean Body wt. | S. Mutans CFU |
|---|---|---|---|---|---|---|---|---|---|---|---|---|---|---|
| | Buccal | | | | Sulcal | | | | Proximal | | | | | |
| Group* | E | Ds | Dm | Dx | E | Ds | Dm | Dx | E | Ds | Dm | Dx | | |
| 1 | 15.8 ± 0.8 | 13.2 ± 0.9 | 9.0 ± 0.8 | 5.8 ± 0.6 | 18.8 ± 1.1 | 14.4 ± 0.7 | 8.6 ± 0.5 | 4.2 ± 0.6 | 7.0 ± 0.4 | 4.8 ± 0.6 | 0.0 | 0.0 | 116 ± 4 | 1.1 × 10[7] |
| 2 | 12.8 ± 0.9 | 10.4 ± 0.7 | 5.0 ± 0.3 | 2.2 ± 0.7 | 15.6 ± 0.7 | 11.8 ± 0.5 | 4.0 ± 0.4 | 1.8 ± 0.2 | 7.4 ± 0.4 | 4.4 ± 1.3 | 0.0 | 0.0 | 117 ± 5 | 6.2 × 10[6] |
| 3 | 15.0 ± 1.0 | 11.4 ± 0.8 | 7.2 ± 0.5 | 4.2 ± 0.7 | 16.4 ± 0.7 | 12.4 ± 0.2 | 4.8 ± 0.4 | 2.0 ± 0.3 | 7.4 ± 0.6 | 5.2 ± 0.6 | 0.0 | 0.0 | 107 ± 5 | 8.6 × 10[6] |
| 4 | 7.8 ± 0.7 | 5.8 ± 0.8 | 3.1 ± 0.5 | 1.2 ± 0.5 | 13.4 ± 0.5 | 10.4 ± 0.4 | 2.8 ± 0.4 | 1.2 ± 0.6 | 4.6 ± 0.8 | 2.4 ± 0.6 | 0.0 | 0.0 | 106 ± 4 | 1.4 × 10[6] |

*1% Test milk in deit 305. All rats infected with S. mutans MT 8148 (serotype c).
[a]Evaluated by the Keys Procedure described in Keyes, P. J., Dental Research, Vol. 37, page 1077 (1958).
E = enamel Ds = dentinal slight Dm = dentinal moderate Dx = dentinal extensive

| 1 | 0 | 0 | 0 | 0 |
|---|---|---|---|---|
| 2 | 0 | 0 | 0 | 0 |

The diet containing chicken IgG antibody against S. mutans caused a reduction in both the dental caries scores and the dental plaque scores (CFU). The avian antibody (chicken IgG) obtained from normal hen eggs had less effect on the caries and/or plaque scores. This experiment demonstrates the use of eggs obtained from chickens immunized against *Streptococcus mutans* for the reduction of dental caires and plaque in the rat model.

EXAMPLE 4

Another embodiment of the invention becomes apparent in this example. The avian antibody effect in mammals can be improved by the simultaneous administration of antibody of mammalian origin. Thus, for example, the use of avian antibody in combination with cow's milk antibody is more effective in treatment of an infection in a mammal than the use of avian antibody alone.

The normal range of antibody consideration in one liter of immune milk is 0.05 to 1 gram of IgG. The addition of an egg to a liter of milk increases the total antibody consideration to 1 to 2 grams.

The experiment described in Example 3 was repeated using cow's milk antibody combined with chicken egg antibody and equivalent doses of just cow's antibody or egg antibody. The results are shown in Table V Group 3.

The combination of chicken and cow antibody produced a greater effect than either the cow or egg antibody alone.

Having now fully described this invention, it will be apparent to one of ordinary skill in the art that many changes and modifications can be made thereto without departing from the spirit or scope of the invention as set forth herein.

What is claimed as new and is intended to be secured by Letters Patent of the United States is:

1. A method of passive immunization of a mammal against a condition caused by an antigen, which comprises:
   (a) feeding said mammal a material, said material comprising heterologous protein antibody, having an enhanced antibody titer against said antigen obtained from the egg of a domesticated fowl immunized against said antigen, until said mammal develops substantial tolerance to said antibody; and
   (b) administering to said mammal an immunologically effective amount of an antibody obtained from a domesticated fowl immunized against said antigen.

2. The method of claim 1 wherein, in said step (a), said mammal is fed whole eggs.

3. The method of claim 1 wherein, in said step (a), said mammal is fed egg yolk.

4. The method of claim 1 wherein, in said step (b), said administration is by injection.

5. The method of claim 1 wherein the condition caused by the antigen is dental caries.

6. The method of claim 1 wherein the condition caused by the antigen is dental plaque.

7. The method of claim 1 wherein, in said step (a), said eggs have an enhanced antibody titer against a multiplicity of antigens including said antigen.

8. The method of claim 1 wherein, in said step (b), said fowl is the same individual as the one used in step (a).

9. The method of claim 1 wherein, in said step (b), said domesticated fowl is a different individual as the one used in said step (a).

10. The method of claim 1 wherein said mammal is a non-human mammal.

11. The method of claim 10 wherein said mammal is selected from the group consisting of a rabbit, a bovid, a horse, a goat, a sheep, an ape, and a monkey.

12. The method of said claim 1 wherein said mammal is a human being.

13. The method of claim 1 wherein said antigen is a bacterial species, product of a bacterial species, or a combination of bacterial species.

14. The method of claim 1 wherein said antigen is a viral species, product of a viral species, or a combination of viral species.

15. The method of claim 1 wherein said antigen is a bioregulatory substance.

16. The method of claim 15 wherein said bioregulatory substance is a hormone, enzyme, or immuneregulatory factor.

17. The method of claim 1 wherein said antigen is a polypeptide.

18. The method of claim 17 wherein said polypeptide is snake venom toxin or bee venom toxin.

19. The method of claim 1 wherein said passive immunization is preventive.

20. The method of claim 1 wherein said passive immunization is paliative.

21. The method of claim 1 wherein, in step (a), said material is fed to said mammal together with material having an enhanced antibody titer against said antigen obtained from the milk of a bovid immunized against said antigen.

22. The method of any of claims 1 or 21 wherein, in step (b), said antibody is administered to said mammal together with antibody purified from milk of a bovid immunized against said antigen, and wherein said combination of antibodies is administered in an immunologically effective amount.

23. The method of claim 22 wherein said administration is by injection.

24. The method of claim 1 wherein said domesticated fowl in steps (a) and (b) is a chicken.

25. The method of claim 1 wherein, in step (b), said antibody is purified from the egg of said domesticated fowl.

* * * * *